(12) United States Patent
Zuccato et al.

(10) Patent No.: US 6,361,789 B1
(45) Date of Patent: Mar. 26, 2002

(54) BIORESORBABLE MATERIAL AND METHOD FOR PRODUCING THE SAME

(75) Inventors: Alessandro Zuccato, Verona; Gabriele Perego, Milan, both of (IT)

(73) Assignee: Sanitaria Scaligera SpA, Verona (IT)

( * ) Notice: Subject to any disclaimer, the term of this patent is extended or adjusted under 35 U.S.C. 154(b) by 0 days.

(21) Appl. No.: 09/051,990

(22) PCT Filed: Oct. 21, 1996

(86) PCT No.: PCT/IT96/00193

§ 371 Date: Aug. 3, 1998

§ 102(e) Date: Aug. 3, 1998

(87) PCT Pub. No.: WO97/15608

PCT Pub. Date: May 1, 1997

(30) Foreign Application Priority Data

Oct. 27, 1995 (IT) .......................................... VR95A0088

(51) Int. Cl.⁷ .................................................. A61F 2/02
(52) U.S. Cl. ...................................................... 424/426
(58) Field of Search ........................... 424/426; 528/354, 528/355

(56) References Cited

U.S. PATENT DOCUMENTS 4,045,418 A 8/1977 Sinclair ................. 260/78.3 R
4,643,734 A * 2/1987 Lin ............................... 623/16
5,633,342 A * 5/1997 Verser et al. ................ 528/355

FOREIGN PATENT DOCUMENTS

EP 628 587 12/1994

* cited by examiner

*Primary Examiner*—Diana Dudash
*Assistant Examiner*—Alysia Berman
(74) *Attorney, Agent, or Firm*—Oppenheimer, Wolff & Donnelly

(57) ABSTRACT

A synthetic material is disclosed, which is constituted by a copolymer of D, L-lactide and ε-caprolactone (which itself is characterized by lower degradation times than those obtainable with copolymers of L-lactic acid and ε-caprolactone), obtained by using as reaction control agent a sugar dianhyide with non-toxic characteristics. The use of suar dianhydrde in the reaction has a considerable control effect on the molecular weight of the copolymer and, thanks to its low molecular weight, this copolymer is characterized by extreraely short resorption times, in the order for the example of one or two months. The copolymer is used as covering clement to be placed around tendon sutures and/or nerve tracts with the aim of preventing formation of scarry adherences between the suture lines and the soft surrounding tissues.

10 Claims, No Drawings

BIORESORBABLE MATERIAL AND METHOD FOR PRODUCING THE SAME

This is a 371 of PCT/IT96/00193 filed Oct. 21, 1996.

TECHNICAL FIELD

The invention relates to a method for obtaining an absorbable or bioresorbable material for use as a covering element in preventing scar adherences.

More in detail, the present invention relates to a method for obtaining a material, provided with relatively short absorption times for the human body, for use as a covering element in a zone where scar adherences might develop, for example in the area around a suture performed on a tendon and/or a nerve tract, as well as internally of the spinal foramen after spinal surgery.

The invention further relates both to the material obtained by the method and to a cladding element for prevention of adherences realised with said material.

The invention finds its principal application in the medical-surgical field.

BACKGROUND ART

The most frequent complication consequent to surgical reconstruction of a tendon and/or a traumatically severed nervous tract is constituted by the formation of scar tissue adherences of the tendon suture line (or of the suture lines of the single nerves belonging to a bundle), with the surrounding soft tissues or the bone surface adjacent to the sutured lesion.

These adherences, which can occur independently of the surgical technique employed in repairing the lesion, can to a considerable degree limit the tendon sliding function, so much so that it is common practice to follow a first surgical operation with a second remedial operation, once the tendon has re-established its biological continuity, to improve tendon excursion: this is particularly common in the field of hand surgery with regard to the flexor apparatus of the hand.

Further, following spinal surgery operations, once the spinal foramen has been opened to afford access to the discs or nervous structures of the rachis, scar tissue forms almost constantly between the osteo-articular surfaces, the muscles around the vertebrae, the endocranial sac and the nerve roots, which limit the small movement that the nerve roots make inside the connecting foramen in order to adapt to the various positions assumed by the spinal column. This movement limitation can lead to painful clinical symptoms which might even be worse than those presented pre-operation and at the origin of the whole intervention.

To obviate the above-mentioned problem, apart from rendering interventions as non-invasive as possible, a practice often employed is that of isolating the nervous structures with free strands of fatty tissue removed from the sottocutaneous area; absorption of the fatty tissue is not, however controllable, and manipulation of same presents some difficulties.

In the field of regeneration of single lacerated nerves, use is made of generally tubular elements acting as guides for the two extremities of a nerve during the regeneration period thereof.

In this context, use is made of nerve guides constituted by non-biodegradable and bioresorbable materials, such as for example silicone rubber (G. Lundborg et al., Exp Neurol. 76 (1982) 361, G. Lundborg et al., Scand. J. Plastic Reconstructive Hand-Surgery 25(1991) 79, G. Lundborg et al. J Neuropathol Exp. Neurol. 41 (1982) 412, M. Merle et al., Microsurg. 10 (1989) 130, B. R. Seckel et al. Plastic Reconstructive Surg. 78 (1986) 793), Acrylic Polymers (B. G. Uzman and G. M. Villegas, J. Neurosci. Res. 9(1993) 157), polyethylene (P. G. Cordeiro et al., Plastic Reconstructive Surg. 83 (1989) 1013) elastomer hydrogel (R. D. Keeley et al., J. Reconstructive Microsurg. 7(1991) (2) 93) or porous stainless steel (W. E. Kuhn and J. L. Hall in "Modern Developments in Powder Metallurgy", edited by H. H. Hausener and P. W. Taubenblat, American Powder Metallurgy Institute, Princeton N.J. p. 279).

The nerve guides, which are synthesised in a non-biodegradable material that remains in situ as a foreign body, can limit the regenerative function of the nerve and give rise to irritation, sometimes years after implantation, in some cases so serious as to necessitate a further operation to remove them.

Also known, in the field of specific application as nerve guides, is the use of biodegradable and bioresorbable material in a predetermined time period, in general comprised between six months and two years.

For example, the prior art teaches use of a copolymer derived from L-lactide combined with poly-$\epsilon$-caprolactone (W. F. A. Den Dunnen et al. in "A new PLLA/PCL copolymer for nerve regeneration", Journal of Materials Science Materials in Medicine 4 (1993) 521–525), G. Perego et al. in "Preparation of a new nerve guide, from a poly(L-lactide-co-6-caprolactone)", Biomaterials 1994, Vol 15 no. 3, 189–193); with like aims an ester of hyaluronic acid (Favaro et al. in "Peripheral Nerve Regeneration Through a Novel Bioresorbable Nerve Guide", ASAIO Transactions 1990 36 (3), M291–M294).

All of the above-mentioned materials have good non-toxic characteristics and low rejection reactions; reabsorption times are relatively long, generally over six months, for which reason these materials are not suitable for other applications requiring much shorter reabsorption times, for example one month.

"An Experimental Study on an Adhesions-Blocking Membrane in the Flexor Tendon of Chicken-Part", Clinical materials 6(1) 1–12 (1990) proposed the use of a membrane realised with a copolymer of leucine-polyeurethane blocks, derived from poly(tetra glycol methylene), toluene diisocyanate and hydrazine.

Copolymers containing 70% leucine were biodegradable in vivo (rat) in about six months, differently to those containing leucine 50%, which were non-biodegradable. From the published data it may be derived that an increase in leucine concentration leads to lower material elasticity and permeability.

For research into adherence inhibition in tendon regeneration it would seem that the 70% leucine composition was chosen as it offered a reasonable compromise between the needs for elasticity, permeability and biodegradability.

It must be remembered however that this material can generate, during degradation, an aromatic amine (toluene diamine), whose toxicity cannot be ignored.

Document U.S. Pat. No. 5350573 describes a method and composition for preventing adhesions during surgical operations. The surface of the tissues and the surgical instruments involved in the operation are covered with a solution of a water-wettable polymer before contacting tissue duringthe operation. The composition comprises a solution of polymer material having a molecular weight of 500000 or above with a weight concentration comprised between 0.01 and about 15%.

Finally, document U.S. Pat. No. 5358973 describes a composition which can be used in surgical operations with the aim of preventing adhesions between tissue surfaces, said composition being an aqueous solution containing dextran and hyaluronic acid.

DESCRIPTION OF THE INVENTION

The present invention provides a method for obtaining a new resorbable material, characterised by extremely brief resorption times, in the order of one or two months, and thus indicated for use as a covering for prevention of adherences, for example tendon sutures and/or nerve tracts, with healing times as indicated above.

This is obtained by carrying out a method having low resorption times, and comprising a copolymersation reaction of D, L-lactide and e-caprolactone, characteted in that a synthesisation is performed using a reaction control agent a sugar dianhydride.

Especially advantageous forms of embodiment of the method according to the invention are characterised by the following The said sugar dianhydride is constituted by 1,4:3,6-dianhydride-(D)-sorbitol or by 1,4: 3,6-dianhydride-(D)-mannitol. Specifically, the 1,4:3,6-dianhydride-(D)-sorbitol is used at a concentration comprised between 0.30% and 0.60%, advantageously 0.44%. Further, the copolymersation reaction is carried out with a presence of a special catalyst; and said catalyst is preferably constituted by tin octanoate. Thus, the sugar dianhydride can be 1,4:3,6-dianhydride-(D)-sorbitol or 1,4:3,6-dianhydride-(D)-mannitol.

The invention also relates to a material obtained using the method of the invention, The resorbable material is for use as a cladding element for prevention of scar adherences between surfaces of tissues subsequent to surgical operations thereon and is characterised in tat said material is constituted by a copolymer of D, L-lactide and $\epsilon$-caprolactone having a molecular weight which is tower than 1 dl/g.

Especially advantageous forms of embodiment of the material according to the invention are that it has a moleculear weight which is about 0.59 dl/g and it is resorbable over a period of time comprised between about one and two months.

Finally, the invention provides an element made of resorbable material which can be used as a covering for prevention of adherences, for example in tendon sutures and/or nerve tracts, This covering element is for prevention of scar adherences between tissue surfaces subsequent to surgical operation, and is characterised in that it is constituted by a material as described above. The covering element is used for prevention of scar adherences between tissue surfaces subsequent to operations for surgical reparation on tendons and/or nerve tracts, as well as for spinal surgery internally of the spinal foramen. The element exhibits a tubular or a flat shape.

This element is described in claims from 10 to 12.

The synthetic material according to the invention is constituted by a copolymer of D,L-lactide and $\epsilon$-caprolactone (which itself is characterised by lower degradation times than those obtainable with copolymers of L-lactic acid and $\epsilon$-caprolactone), obtained by using as reaction control agent a sugar dianhydride with non-toxic characteristics, and thus suitable for the purposes of the invention.

Experiments carried out by the applicant have surprisingly revealed that the use of sugar dianhydride as a control agent resulted in a copolymer with very low inherent viscosity (thus having a low molecular weight), in the example much lower than viscosities of similar copolymers obtained without the use of sugar dianhydride.

Therefore the use of sugar dianhydride in the reaction has a considerable control effect on the molecular weight of the copolymer and, thanks to its low molecular weight, this copolymer is characterised by extremely short resorption times, in the order for example of one or two months.

Such resorption times are decidedly lower than those obtained using known-type similar materials, and can be compared to those obtained by means of other biomaterials, such as hyaluronic acid, modified or not, which does not have the often-advantageous chemical-physical and mechanical properties of aliphatic polyesters, such as lactic acid copolymers.

Therefore the material according to the invention is advantageous inasmuch as it is constituted by homo- and copolymers of lactic acid with controlled molecular weight, with the help of a non-toxic agent for control of the reaction.

According to a form of embodiment of the invention, the copolymer of lactic acid was obtained by synthesising D,L-lactide and $\epsilon$-caprolactone in the presence of tin octanoate as catalyst and using 1,4:3,6-dianhydride-(D)-sorbitol at 0.44% concentration.

More precisely, L-lactide was synthesised from D,L-lactic acid at 90% (Fluka, Buchs, CH); 1000 ml of D,L-lactic acid were placed in a two-litre two-neck flask, and heated gradually to 200° C., contemporaneously distilling the water formed by the reaction.

The viscous product thus obtained was depolymerised in the presence of a tin powder catalyst, at a temperature of 200° C. and 0.1 Torr, contemporaneously distilling the D,L-lactide formed by the reaction.

The raw lactide thus obtained was recrystallised three times by methyl isobutyl ketone, obtaining thus 385 g of white crystalline product, having a fusion temperature of 124–126° C.

The preparation was completed with a final drying stage at 45° C. and 0.1 Torr for 24 hours.

Subsequently the $\epsilon$-caprolactone (Fluka) was dried on $CaCl_2$ distilled at reduced pressure and conserved in nitrogen.

The 1,4:3,6-dianhydride-D-sorbitol (Fluka) was recrystallised using ethyl acetate, dried at 45° C. and 0.1 Torr for 24 hours, and conserved in nitrogen.

The tin octanoate (Sigma) was conserved in nitrogen on activated molecular sieves and used without further purification treatment. The copolymerisation was carried out in a nitrogen atmosphere in a 100 ml two-neck flask, in which 118.89 g of D,L-lactide, 50.95 g of $\epsilon$-caprolactone equal to 47.4 ml, 0.743 g of 1.4:3,6-dianhydride-D-sorbitol and 0.100 g of tin octanoate were located in dry-box conditions.

The copolymerisation reaction was protracted for 7 hours at a temperature of 150° C., whereafter the flask was left to return to atmospheric temperature.

The material was rubbery and transparent.

The copolymer obtained in this way exhibits an inherent viscosity of 0.59 dl/g, measured in chloroform at 25° C., considerably lower than the viscosity values (generally comprised between 2.5 and 3.5 dl/g) normally obtained for the same copolymer in the absence of molecular weight control agents.

A material having low resorption times, in the order of one or two months, is well adapted to use in setting up a surgical method for covering tendon sutures and/or nerve tracts with the aim of preventing formation of scarry adherences between the suture lines and the soft surrounding tissues.

To this end, the suture zone is enveloped in a covering element made of a material having a low resorption time, which isolates the sutured segment from the surrounding tissues for a period of time which is limited to the completion of the healing processes.

The covering element can be constituted by a sheet of resorbable material, cell-proof, or by a tubular element internally of which an extremity of the operable tendon or nerve tract is inserted before surgical intervention, and which is arranged above the suture zone after the operation for connecting the ends of the tendon and/or the nerve tract.

Experiments carried out by the applicant have demonstrated that a low-resorption time material, such as for example the copolymer of lactic acid obtained with the sugar dianhydride control agent of the invention can advantageously be used in carrying out a method such as the one described above.

The covering element made from low-resorption times material has in fact been shown to be non-toxic, non-interacting with the healing processes, and resorbable in a considerably shorter time than that needed by a like-composed material obtained without the control agent.

For example, the applicant carried out an in vivo experimental study on an animal. The experiment was on chicken deep digital flexor. Chicken was chosen as best for the purpose, because:

it has a digital flexor apparatus which anatomically similar to Human, and the sizes are suitable for surgical treatment;

the biological processes consequent to surgical lesion and healing are known and sufficiently close to those of Human;

a valid flexion response can be obtained from mechanical stimulation of Chicken (by applying the palm of the claw to a cylindrical bar of suitable dimensions and rotating the bar, causing a constant prehensile response with powerful digit flexion), so that the possible flexion range could be measured.

The study was carried out on three groups of animals.

The first group was used to evaluate the biological aspects of tendon repair in an isolated environment. It was constituted by five animals, who were subjected under general anaesthetic to traumatic lesion of the flexor apparatus of the second digit of each claw. The wound was palm-transversal throughout, interesting the skin, subcutaneous level, flexor tendons up to the bone of the median phalanx.

Subsequently the animals were operated, with a longitudinal lateral incision of the digit and raising of the palm cutaneous flap, avulsion of the surface flexor tendon up to bone insertion, repairing of the deep flexor by modified Bunnell technique with single thread suture Prolene 4-0, and covering of the tendon in a tube of material according to the invention, extending by 1 cm proximally and distally of the tendon suture line.

The claws were immobilised in a plaster-of-paris cast with the operated claw arranged in a three-quarters of total flexion excursion.

The animals were sacrificed respectively at 1, 2, 3, 4 and 6 weeks after the operation, the claws amputated and the regions operated subjected to a histological study to evaluate the extent of biological reparation in the various phases, as well as to check for presence and characteristics of any scar adherences around the tendon.

The findings could then be compared with those relating to the numerous existing studies on tendon lesion healing in the absence of interplaced material.

The second and the third groups were respectively constituted by five animals each.

The animals were subjected to trauma and surgical treatment similar to that of the first group, with the difference that for the animals of the second group no interposing material was used.

The animals of the two groups were thus healed, and the cast removed five weeks after the operation, and the flexion capacity of the operated digit evaluated using the above-described method of the cylindrical bar immediately after removal of the cast and in the two following weeks.

Digital flexion of the two groups was compared to evaluate the degree of usefulness of the material according to the invention.

From the experiments it was found that there is a total absence-of adherences and an almost total resorption of the material of the invention.

The invention has been described herein with reference to some preferred embodiments thereof.

However, it is clear that the invention is not absolutely limited to the above-described embodiments, and that it comprises numerous variations which belong in the scope of the invention, specifically with regard to the composition of the low-resorption-times materials.

Low resorption times materials, both in lactic acid copolymer form as in the above-described material, and in other types of aliphatic polyester with especially short resorption times, such as for example copolymers derived from glycol and $\epsilon$-caprolactone, that is, using glycolic acid in the place of lactic acid, and derivatives of hyaluronic acid.

With regard to the covering element made using such a material, it is clear that it can be made both in a tubular shape and in a leaf which can be enveloped about the suture zone.

What is claimed is:

1. A method for obtaining a resorbable material having low resorption times, comprising a copolymerisation reaction of D, L-lactide and $\epsilon$-caprolactone using 1,4:3,6-dianhydride-(D)-sorbitol to control at least one parameter from the group consisting of the viscosity or molecular weight of the copolymer.

2. A method as in claim 1, wherein the 1,4:3,6-dianhydride-(D)-sorbitol is used at a concentration between about 0.30% and about 0.60% by weight.

3. A method as in any one of the preceding claims, wherein the copolymerisation reaction is carried out with a presence of a tin catalyst.

4. A method as in claim 3 wherein the tin catalyst is tin octanoate.

5. A method as claimed in claim 2 wherein the concentration is about 0.44% by weight.

6. A method for obtaining a resorbable material having low resorption times, comprising a copolymerisation reaction of D, L-lactide and $\epsilon$-caprolactone, comprising using a sugar dianhydride as an agent to control at least one parameter selected from the group consisting of the viscosity or molecular weight of the copolymer.

7. A method for obtaining a resorbable material having low resorption times, comprising a copolymerisation reaction of D, L-lactide and $\epsilon$-caprolactone, comprising using a sugar dianhydride as &i agent to control, at least one parameter selected from the group consisting of the viscosity or molecular weight of the copolymer, characterised in that the sugar dianhydride is selectively 1,4:3,6-dianhydride-(D)-sorbitol or 1,4:3,6-dianhydride-(D)-mannitol.

8. A method as in claim 7, wherein the 1,4:3,6-dianhydride-(D)-sorbitol is used at a concentration between about 0.30% and about 0.60% by weight.

9. A method as in any one of the claims 7 or 8, wherein the copolymerisation reaction is carried out with a presence of a tin catalyst.

10. A method as in claim 9, wherein the tin catalyst is tin octanoate.

* * * * *